United States Patent [19]

Domankevitz et al.

[11] Patent Number: 5,571,098
[45] Date of Patent: Nov. 5, 1996

[54] LASER SURGICAL DEVICES

[75] Inventors: Yacov Domankevitz, Brookline; Norman S. Nishioka, Wayland, both of Mass.

[73] Assignee: The General Hospital Corporation, Boston, Mass.

[21] Appl. No.: 332,942

[22] Filed: Nov. 1, 1994

[51] Int. Cl.$^6$ ........................................... A61B 17/36
[52] U.S. Cl. ............................ 606/15; 606/39; 606/45
[58] Field of Search ........................ 606/2, 10, 11, 606/12, 13, 14, 15, 16, 17, 27, 28, 29, 33, 37, 38, 39, 40, 41, 45, 46, 47, 48, 49, 50, 51, 52

[56] References Cited

U.S. PATENT DOCUMENTS

| | | | |
|---|---|---|---|
| 4,126,136 | 11/1978 | Auth et al. | 128/303.1 |
| 4,185,633 | 1/1980 | Prozorov et al. | 128/303.1 |
| 4,240,431 | 12/1980 | Komiya | 606/15 |
| 4,273,127 | 6/1981 | Auth et al. | 128/303.1 |
| 4,625,435 | 12/1986 | Hoskin | 606/16 |
| 4,627,435 | 12/1986 | Hoskin | 128/303.1 |
| 4,638,800 | 1/1987 | Michel | 128/303.1 |
| 4,651,734 | 3/1987 | Doss et al. | 128/303.14 |
| 5,085,657 | 2/1992 | Ben-Simhon | 606/42 |
| 5,147,356 | 9/1992 | Bhatta | 606/37 |
| 5,180,378 | 1/1993 | Kung et al. | 606/10 |
| 5,254,115 | 10/1993 | Bhatta et al. | 606/16 |

FOREIGN PATENT DOCUMENTS

WO92/06641  4/1992  WIPO ...................... A61B 17/36

OTHER PUBLICATIONS

Doty et al., "The Lacer Photocoagulating Dielectric Waveguide Scalpel," IEEE, BME–28:1–9, 1981.
Gorisch et al., "Heat–Induced Contraction of Blood Vessels," Lasers in Surgery and Medicine 2:1–13, 1982.
Unknown, "Laser blade offers new surgical tool," C&EN, pp. 24–25, 1978.

Primary Examiner—Angela D. Sykes
Assistant Examiner—Sonya Harris-Ogugua
Attorney, Agent, or Firm—Fish & Richardson P.C.

[57] ABSTRACT

A method and device for first irradiating a region of tissue with a radiation source, and then incising the region with a mechanical cutting instrument (e.g., a scalpel). Irradiation allows for effective heating of the tissue, which results in blood vessel contraction or coagulation of the blood before the actual incision is made; once the tissue is incised, the resulting flow of blood is low.

23 Claims, 4 Drawing Sheets

LASER SURGICAL DEVICES

This invention was made with Government support under Contract #N00014-91-C-0084 awarded by the Office of Naval Research. The Government has certain rights in this invention.

BACKGROUND

This invention relates to surgical instruments, and to lasers used in such instruments.

During a surgical procedure, it is usually desirable to reduce the amount of blood discharged from an incised region of tissue. Application of radiation to the tissue following the incision results in coagulation, thereby reducing the amount of bleeding once the incision has been made.

Light sources, such as lasers, can be coupled to optical fibers and used to irradiate and heat the incised region in a controllable manner. Using this procedure, light of the appropriate wavelength is absorbed by the various components of the tissue, and optical energy is converted into thermal energy to heat and coagulate the incised region.

In principle, light sources can be combined with surgical instruments in two ways: in one method, the light source can be used in combination with a mechanical cutting device, such as a scalpel, and used to illuminate recently incised tissue. Such "laser scalpels" allow heating of tissue regions following, or in some cases during, the surgical procedure. Devices of this kind are described in U.S. Pat. Nos. 4,249,533; 4,266,577; and 4,195,633, among others. Alternatively, the light source can be used as a source for both ablation and coagulation. In this technique, ablation of tissue using high levels of radiation often results in undesirable tissue-containing plumes, which must be contained (typically with smoke-evacuation systems) during the procedure.

SUMMARY

We have discovered that superior control of blood loss associated with surgery can be achieved by causing coagulation of blood in a region prior to cutting of that region. Accordingly, in one aspect, the invention provides a surgical instrument including a mechanical cutting device having cutting means for making an incision in a mammal, and a radiation source which is connected to the mechanical cutting device. The radiation source is configured to irradiate and heat a region in front of the cutting means during incision so as to induce coagulation therein prior to incision.

The radiation source is preferably an optical waveguide (e.g., a single optical fiber, a planar waveguide, or a fiber optic bundle) coupled to a light source; alternatively, the radiation source may be a microwave waveguide coupled to a microwave radiation generator. The term "coupled", as used herein, is meant that the radiation is delivered from the radiation source to the waveguide. The radiation source allows for effective heating of tissue, preferably to a temperature of at least 60° C. Heating results in contraction of blood vessels, or coagulation of the blood, resulting in a minimization of blood loss during the incising process. Ablation may also be induced during the incising process by heating of the tissue.

Most preferably, the light source is a laser, such as an ion (e.g., an argon ion), solid-state (e.g., diode, holmium, Nd:YAG, or Ti:sapphire), excimer, dye, $CO_2$, or metal-vapor laser. Alternatively, a flashlamp may be used as the light source; in this case, the flashlamp is preferably used with optical filters to allow selection of the appropriate wavelength of light. In alternate embodiments, the light source is used to directly irradiate the region to be incised without using an optical waveguide. In this embodiment, the light source is preferably a diode laser.

The surgical instruments of the present invention may be used during any procedure in which a conventional surgical instrument is normally used. Preferably, the mechanical cutting device used for incision is a scalpel, surgical scissors, or a dermatome.

The method of the invention is carried out using a surgical instrument where the radiation source is connected to the handle of the mechanical cutting device. In this case, the handle is angled relative to the cutting means of the instrument so that the radiation source irradiates a region in front of the cutting means to induce coagulation therein prior to incising the region.

In yet another aspect, the invention provides a method for incising a selected region of a mammal which includes the steps of irradiating the region to induce coagulation therein, and then incising the region.

The inventions have many advantages. The surgical instruments of the invention are particularly effective in controlling blood loss in procedures normally resulting in excess bleeding, such as liver resection, removal of skin eschar, and tumor excision.

DETAILED DESCRIPTION

Figure 1A:
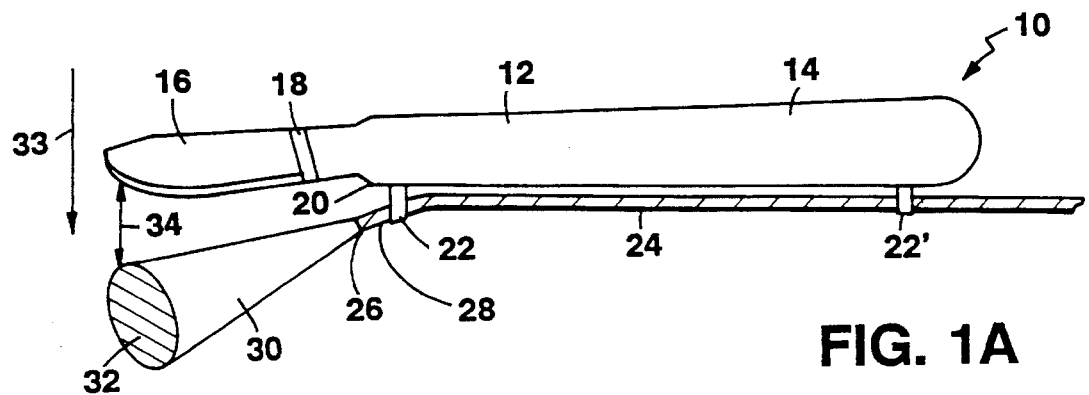
FIGS. 1A–1C are side views of a laser scalpel of the invention.

Referring to FIG. 1A, a laser scalpel 10 includes a mechanical cutting device 12 which contains a handle 14 and a blade 16 for making the incision. Typically, these components are made of durable, non-oxidizing metals, such as stainless steel or aluminum. A connecting portion 18 allows the blade 16 to be easily removed, and replaced if necessary. The mechanical cutting device 12 may be a scalpel of any type; other mechanical cutting devices known in the art, such as surgical scissors and dermatomes, may be used with the present invention.

Using mounts 22, 22' (preferably made of metal or plastic-based materials) an optical fiber 24 (or other optical waveguide) is attached to the side 20 of the mechanical cutting device 12 to allow delivery of light from a light source (not shown in the figure) to the distal end 26 of the optical fiber 24. Alternatively, a planar waveguide, fiber optic bundle, or other fiber optic device may be used in place of the optical fiber. In all cases, the elements used to deliver light are composed of materials commonly used in the optical fiber arts, i.e., silica, silica-based, or polymer-based fibers, each containing a core region (typically having a refractive index of about 1.4) and a cladding region having a relatively high refractive index to allow for propagation of the optical field via total internal reflection in the fiber. Multi-mode, polarization-scrambling fibers and fiber optic bundles available, for example, from Fiberguide, Industries (Sterling, N.J.) may be used for light delivery. In general, the diameter of the fiber should be large enough to allow significant coupling of the optical field emitted from the light source, while being small enough to allow the fiber to retain flexibility during operation. If a fiber optic bundle is used, each fiber preferably has a diameter of between about 5 and 500 μm, and is surrounded with a polymer (e.g., polyimide) jacket for mechanical stability. The fiber 24 is attached to the mechanical cutting device 12 in such a way that it does not interfere with the gripping or operation of the device.

During the irradiation step, light is preferably coupled into the proximal end of the fiber (not shown in the figure) and propagates until it arrives at the distal end 26, where it is delivered to the region of interest. Near the tip of the distal end 26, the fiber 24 may contain a bent region 28 which allows the emitted optical field 30 to irradiate a region 32 in front of the cutting surface of the blade 16; absorption of the optical field 30 induces heating of the region 32 to cause coagulation in the underlying tissue. During operation, the blade is moved in the direction indicated by the arrow 33, and recently coagulated tissue is incised. By changing the angle between the fiber and the cutting surface of the blade, the distance (indicated in FIG. 1A by the vertical line 34) separating the blade 16 and the region 32 can be adjusted, thereby allowing the time period separating the illumination and incision steps to be selectively controlled.

Figure 1B:
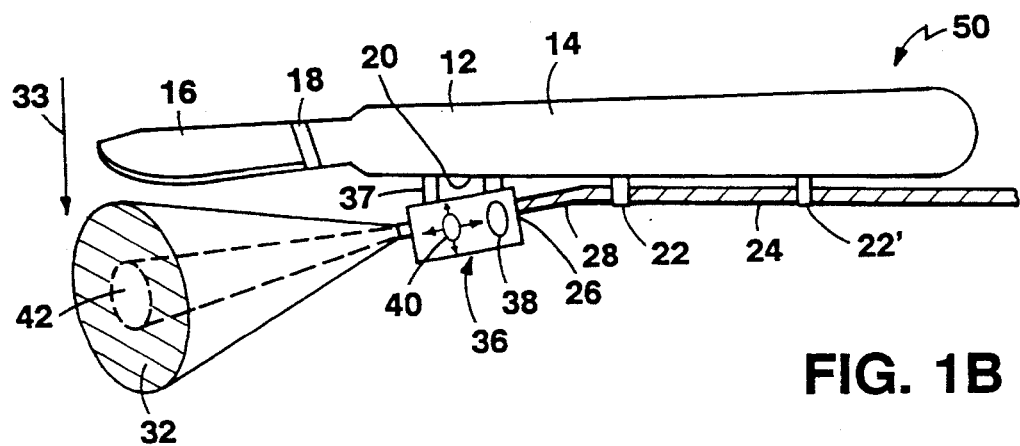

Referring now to FIG. 1B, in another embodiment of the invention, a laser scalpel 50 includes a optical fiber 24 having a distal tip 26 inserted into a housing 36 attached to the scalpel handle 14 using clamps 37, 37'. The housing 36 contains a series of lenses 38, 40 used for focussing or expanding the beam. In this embodiment, for example, the optical field emerging from the distal fiber end 36 is incident on a stationary lens 38, where the light is roughly collimated. Adjustment of the axial position of a second lens 40 allows the resultant optical field to be condensed or dispersed, thereby allowing the size of the illuminated region 32 to be controlled. The lens 38 can be adjusted so that the optical field is focussed, resulting in a smaller region 42 of illumination. In such embodiments, the second lens 40 may be a cylindrical lens, rather than a spherical lens, which illuminates a more elliptical region of tissue. Alternatively, the tip of the fiber 24 can be tapered, or made dome-shaped, so that the emerging light is focussed without the use of external lenses. The size of the illuminated region can be adjusted by changing the position of the distal end of the optical fiber relative to the region undergoing illumination.

Figure 1C:
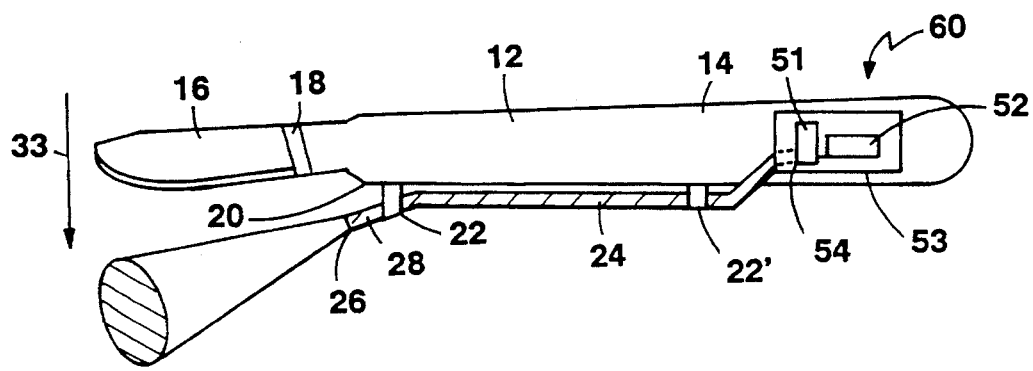

In other embodiments, the light source can be included on the handle of the scalpel, thereby increasing the mobility of the surgical instrument. Referring now to FIG. 1C, a light source 51 and battery 52 are contained in an optical housing 53 attached directly to the handle 14 of the scalpel 12. The proximal tip 54 of the fiber 24 is interfaced directly to the light source 51 and enclosed in the optical housing 53. Preferably, in this embodiment, the light source 51 is a laser diode; other small-scale light sources may also be used. Illumination and incision using the laser scalpel 60 is then carried out as previously described.

In related embodiments, the laser is a diode laser (or another small-scale light source), and is attached near the incising surface and used to directly illuminate the tissue without first passing through an optical waveguide. In such embodiments, the laser may be attached to a galvanometer, or used in combination with reflecting optics attached to a galvanometer, to allow the beam to be scanned in a horizontal or vertical direction relative to the incising direction to heat a larger region of tissue.

Figure 2A:
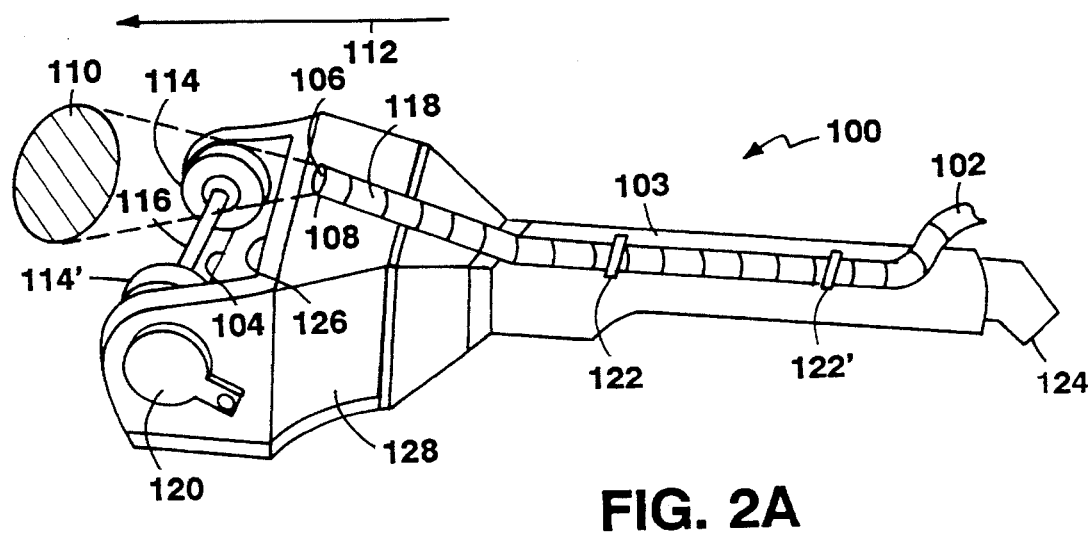
FIGS. 2A and 2B are, respectively, side and front views of a laser dermatome of the invention.
Figure 2B:
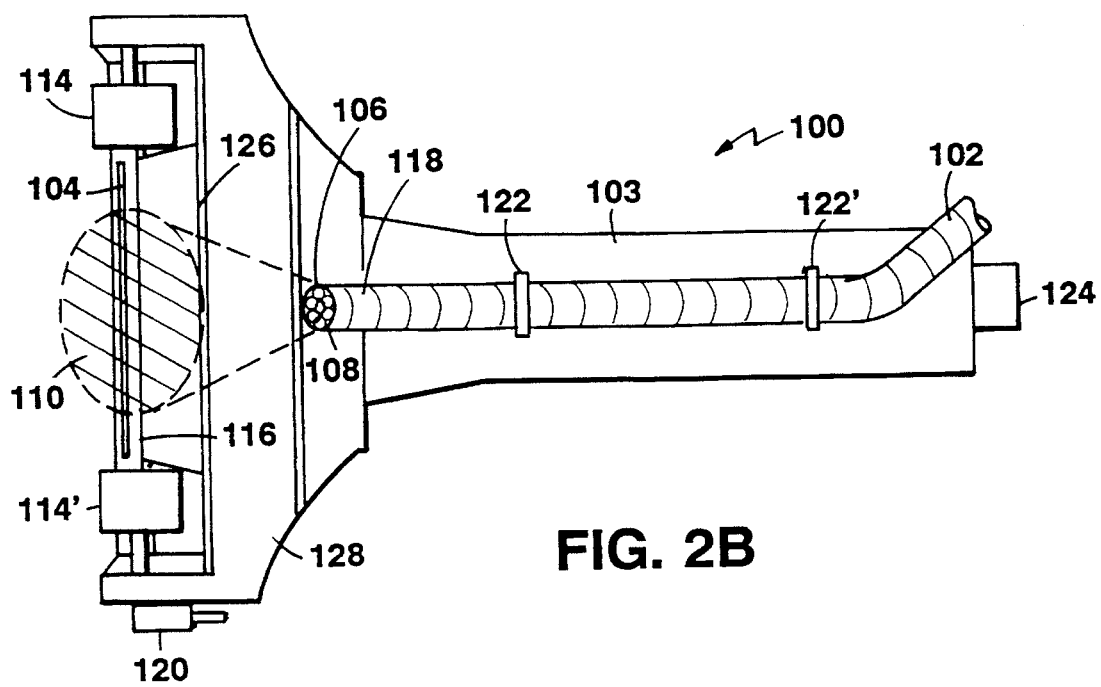

Referring now to FIGS. 2A and 2B, a laser dermatome 100 according to the invention contains an optical fiber 102 attached to a handle 103 using mounts 122, 122', and a incising blade 104 used for shaving skin layers from a patient, such as a burn victim. Alternatively, the fiber 102 may be received by the dermatome 100 at a port 124, thereby allowing it to be housed internally; in such embodiments, the distal end 108 of the fiber 102 is located in the interior section 126 of the front housing 128 of the dermatome 100. Other methods of internally housing the optical fiber may also be used according to the invention.

The angle of the shaving blade 104 and the depth of the corresponding cut can be adjusted with a rotatable knob 120. During operation, radiation from a light source (not shown in the figure) is coupled into the proximal end of the fiber 102, where it propagates to the distal end 108 and emerges to irradiate and heat a region 110 in front of the shaving blade 104. The distance separating the distal end 108 of the fiber 102 and the tissue surface is chosen so that the illuminated region 110 has similar width to that of the shaving blade 104. The fiber 102 may contain a bent region 118 positioned at an angle relative to the shaving blade 104 which allows the distance separating the blade and the illuminated region 110 to be increased or decreased; this allows the time period separating illuminating and incising steps to be adjusted. In alternate embodiments, a series of lenses (preferably cylindrical lenses) can be adapted to the distal end 108 of the fiber 102 so that a wider region 110 can be illuminated. Alternatively, individual optical fibers contained within a fiber optic bundle may be used to illuminate the tissue to be incised; these fibers may be arranged in a linear, rather than circular, fashion so that a linear region on the tissue surface is illuminated.

In order to shave layers of skin, the dermatome 100 is moved along the direction indicated by the arrow 112 with the assistance of roller wheels 114, 114' mounted on a bar 116 attached to the interior section of the front housing 128. In general, the dermatome coupled with the light source may be used during any procedure in which a conventional dermatome is normally used.

Figure 3A:
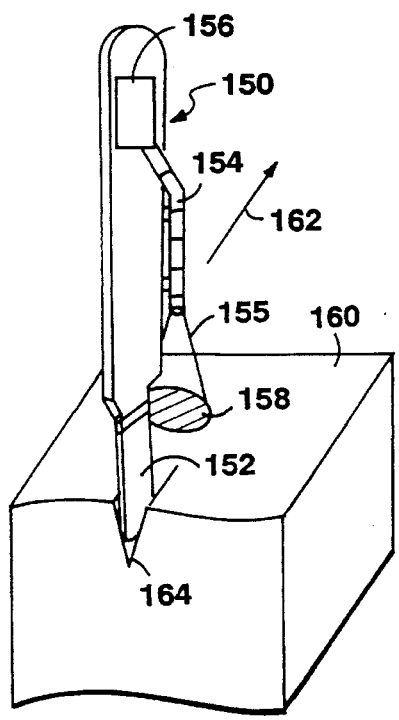
FIGS. 3A and 3B are, respectively, illustrations of incisions being made with a laser scalpel and a laser dermatome in accordance with the invention.
Figure 3B:
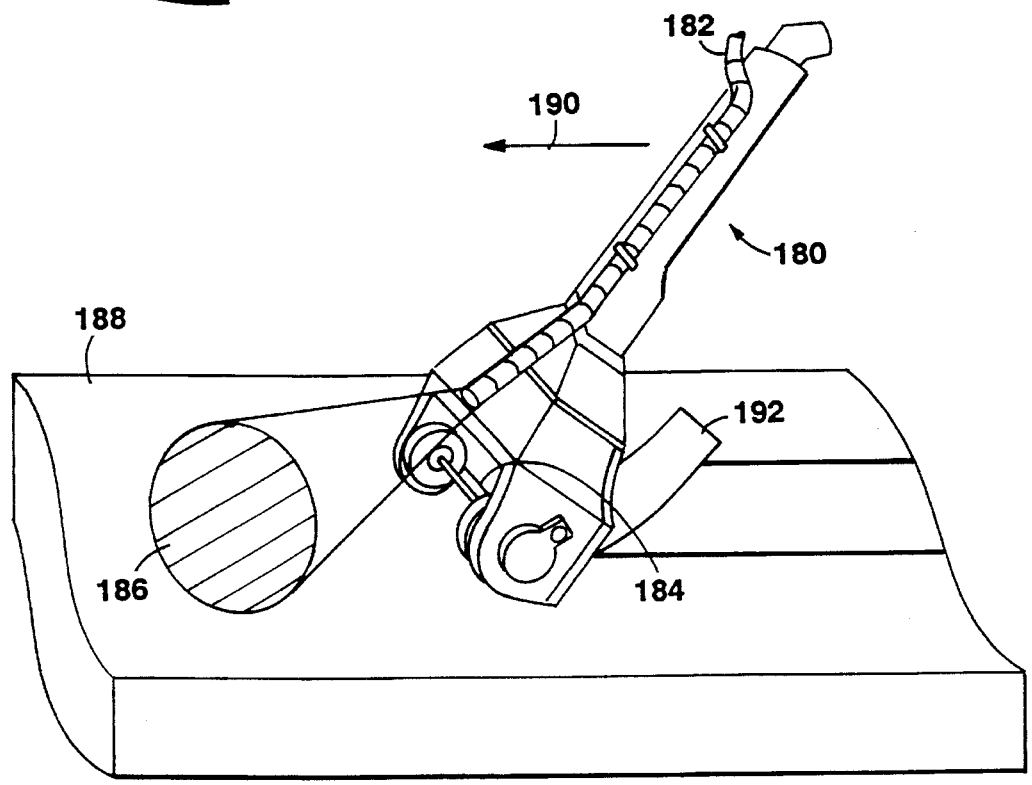

Referring now to FIGS. 3A and 3B, a laser scalpel 150 contains a blade 152 and an optical fiber 154 which allows optical radiation 155 to be delivered from a light source 156 to a region 158 on the surface of a tissue 160. When the scalpel 150 is moved along the tissue 160 in the direction indicated by the arrow 162, optical radiation 155 first heats the region 158 of the tissue, causing coagulation, thereby minimizing blood flow once a cut 164 is made in the region. In other embodiments, a laser dermatome 180 containing an optical fiber 182 and a incising blade 184, and moving in a direction indicated by an arrow 190 along a skin surface 188, allows a region 186 of the surface 188 to be illuminated and heated. This induces coagulation in the underlying vasculature, thereby reducing the amount of blood flow once a layer 192 of skin is removed from the skin surface 188.

Figure 4:
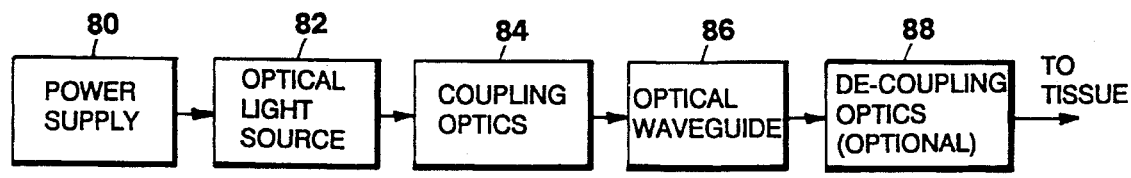
FIG. 4 is a block diagram listing the optical and electrical components of the invention.

Referring now to FIG. 4, the optical and electronic components of a light source used in accordance with the invention include a power supply 80 to supply voltage to the light source 82, which is most preferably a laser. Depending on the surgical procedure, the light source may be a single laser, a secondary laser pumped by a primary laser, or a primary laser having an output which is further amplified.

Preferred lasers include ion, dye, solid-state (e.g. Nd:YAG and Ti:sapphire), holmium, $CO_2$, copper-vapor, excimer, and diode lasers. Flash lamps, optionally used in combination with optical filters, may also be used to generate the optical field. The field may then be coupled into a fiber optic device 86, such as a single fiber or a fiber optic bundle, using a series of coupling optics 84 which may include a series of lenses (such as microscope-objective or small-focal-length lenses) which condense the optical field to a spot size roughly equivalent to the core diameter of the fiber. Following coupling, the field propagates through the fiber-optic device 86 until it emerges from the distal end; at this point, the spatially dispersing field may require de-coupling optics 88 (i.e., a second series of lenses) to collimate the emerging beam. Microwave cavities may also be used, although in this case the coupling 84 and decoupling 88 optics are replaced with microwave couplers, and the fiber optic device 86 is replaced with a microwave waveguide device.

Control over the parameters of the optical field allows adjustment of the amount of heat (and associated coagulation or vascular constriction) induced in the tissue prior to incision. In particular, the wavelength, intensity, time dependence, and spatial mode of the optical field can all be adjusted to vary the heating of the region. The parameters of the optical field should be chosen so that sufficient heat-induced coagulation occurs during the time period separating the illuminating and incising steps. If not enough heat is delivered to the tissue, coagulation in the underlying tissue may be insufficient; too much heating may impart excess thermal damage to the tissue. In order to select the appropriate wavelength and intensity of the light source, properties of the tissue, such as the wavelength-dependent reflection R and absorption $\alpha$, density $\rho$, heat capacity C, and thermal diffusivity $\kappa$, should be considered. In general, following optical absorption, the expected temperature rise ($\Delta T$) at the tissue surface is $$\Delta T = 1/\rho C \, P_a (1-R) I \alpha \qquad (1)$$

where Pa is the fraction of light intensity I converted into heat; following the rise in temperature, heat is conducted away from the tissue surface with a time dependence described by standard heat diffusion equations. Typically, in accordance with the invention, the underlying tissue is heated to a temperature of at least 60° C.

Figure 5:
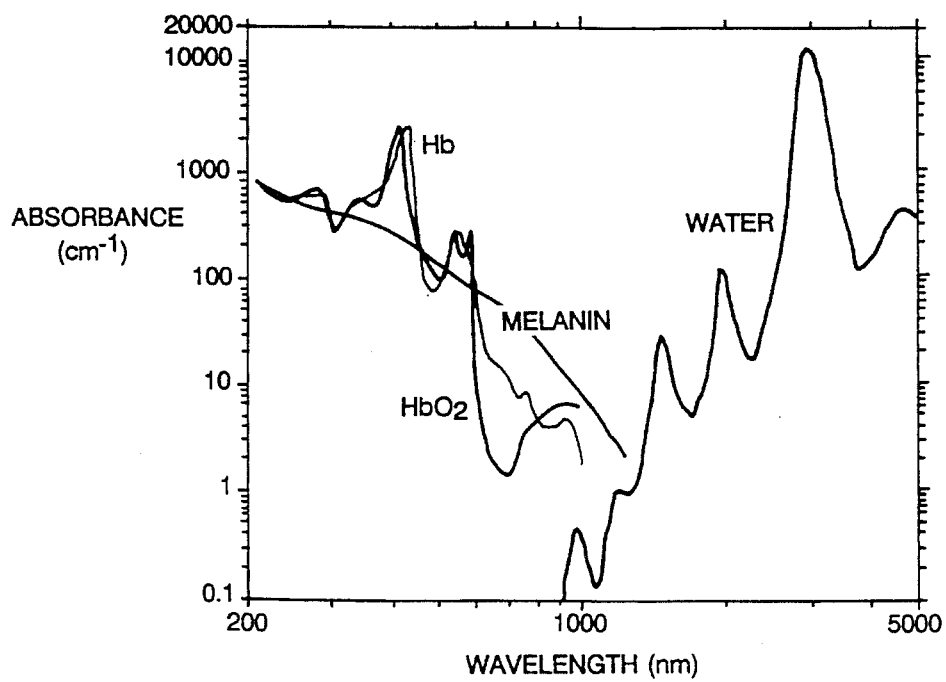
FIG. 5 is a plot showing the optical absorption spectra of melanin, hemoglobin, and water.

Referring now to FIG. 5, the absorption spectra of several chemical components (i.e., hemoglobin (Hb), oxidized hemoglobin ($HbO_2$), melanin, and water) present in different types of tissue illustrate the ability of these compounds to absorb optical radiation to generate coagulation-inducing heat. For example, wavelengths in the blue-green spectral region (i.e., between 400 and 550 nm), such as those emitted from argon ion lasers (514 nm) or frequency-doubled Nd:Yag (532 nm) or Ti:sapphire (400–500 nm) lasers, will be rapidly absorbed by hemoglobin contained in the blood. These light sources will be effective in heating and inducing coagulation in highly vascularized tissue, such as tumors and the liver.

Light in the infrared spectral region (i.e., 700–11,000 nm) may also be used in accordance with the invention as it is absorbed by the water present in nearly all types of tissue. In particular, light sources such as holmium-based (e.g., holmium:Nd) (2100 nm), Nd:YAG (1064 nm), Ti:sapphire (800–1100 nm), $CO_2$ (10.6 µm) and diode lasers (700–1500 nm) will be effective in heating the water in tissue to induce coagulation in neighboring blood vessels. In alternate embodiments, topical application of a highly absorbing substance, such as a tissue-compatible dye (e.g., indocyanine green or methylene blue), can be used to increase the optical absorption of a region of tissue to increase the amount of heating and coagulation.

In addition to selecting the appropriate wavelength, the optical intensity delivered to the region can be adjusted to vary the level of heating. Techniques known in the art, such as varying the power supplied to the light source, attenuating the intensity of the optical field before (or after) propagation through the fiber, or decreasing the coupling of the emitted optical field into the optical fiber, can all be used to adjust the amount of delivered radiation.

In other embodiments of the invention, the time dependence of the optical field can be varied to adjust the amount of heat deposited in the region. For example, light sources which are pulsed (i.e., those which emit discrete pulses of light, rather than continuous, time-independent optical fields) have a peak power which is inversely related to the pulse duration; as the pulse becomes shorter, the peak power increases, resulting in a more rapid heating of the tissue. In this case, pulses having a broad range of durations, i.e., between about 50 femtoseconds and hundreds of milliseconds, may be delivered to the tissue.

In another embodiment of the invention, the spatial intensity profile of the optical field can be adjusted to vary the amount of heat delivered to the region of interest; light from the fiber can be either condensed, spatially dispersed, or modulated using other means known in the art to adjust the region illuminated by the optical field.

In still other embodiments, neither the light source or optical fiber is attached to the mechanical cutting device, and the region of tissue to be incised is first illuminated with a separate device containing an optical fiber or an equivalent light-delivery device; a mechanical cutting device is then used to incise the illuminated regions. In other embodiments, imaging optics may be used in combination with the invention to allow for visualization of the area being incised. Such optics may include fibers within the fiber-optic bundle used for light delivery.

Other embodiments of the invention are within the scope of the following claims.

What is claimed is:

1. A method for incising a region of a mammal with a cutting means, comprising the steps of:

irradiating said region and not said cutting means to induce coagulation in said region, and then incising said region.

2. The method of claim 1, wherein said irradiating is carried out using optical or microwave radiation.

3. The method of claim 2, wherein said optical or microwave radiation is absorbed by said region to heat said region and induce coagulation therein.

4. The method of claim 2, wherein said radiation is optical radiation produced by a laser.

5. The method of claim 4, wherein said laser is selected from the group consisting of diode, Nd:YAG, Nd:YLF, holmium, Ti:sapphire, ion, excimer, dye, $CO_2$, and metal-vapor lasers.

6. The method of claim 4, wherein said optical radiation is produced by a flashlamp.

7. The method of claim 1, wherein said incising is carried out using a mechanical cutting device.

8. The method of claim 7, wherein said mechanical cutting device is a scalpel.

9. The method of claim 7, wherein said mechanical cutting device is surgical scissors.

10. The method of claim 7, wherein said mechanical cutting device is a dermatome.

11. A surgical instrument, comprising:

a mechanical cutting device including cutting means for making an incision in a region in a mammal; and a radiation source connected to said mechanical cutting device, said radiation source being configured to irradiate a region to be incised in front of said cutting means and not said cutting means so as to induce coagulation in the region prior to incision thereof.

12. The surgical instrument of claim 11, wherein said radiation is optical radiation.

13. The surgical instrument of claim 12, wherein said radiation source is an optical waveguide coupled to a light source.

14. The surgical instrument of claim 13, wherein said light source is a laser.

15. The surgical instrument of claim 14, wherein said laser is selected from the group consisting of diode, Nd:YAG, Nd:YLF, holmium, Ti:sapphire, ion, excimer, dye, $CO_2$, and metal-vapor lasers.

16. The surgical instrument of claim 13, wherein said light source is a flashlamp.

17. The surgical instrument of claim 12, wherein said radiation source is a laser attached directly to said mechanical cutting device.

18. The surgical instrument of claim 17, wherein said laser is a diode laser.

19. The surgical instrument of claim 11, wherein said radiation source is a microwave waveguide coupled to a microwave radiation generator.

20. The surgical instrument of claim 11, wherein said mechanical cutting device is a scalpel.

21. The surgical instrument of claim 11, wherein said mechanical cutting device is surgical scissors.

22. The surgical instrument of claim 11, wherein said mechanical cutting device is a surgical dermatome.

23. A surgical instrument, comprising:

a mechanical cutting device including a handle and cutting means for making an incision in a region in a mammal; and a radiation source connected to said handle and angled relative to said cutting means to irradiate a region to be incised in front of said cutting means and not said cutting means so as to induce coagulation in the region prior to incision thereof.

* * * * *